United States Patent [19]
Nikiforov et al.

[11] Patent Number: 5,518,900
[45] Date of Patent: May 21, 1996

[54] METHOD FOR GENERATING SINGLE-STRANDED DNA MOLECULES

[75] Inventors: Theo T. Nikiforov; Michael R. Knapp, both of Baltimore, Md.

[73] Assignee: Molecular Tool, Inc., Baltimore, Md.

[21] Appl. No.: 155,746

[22] Filed: Nov. 23, 1993

Related U.S. Application Data

[63] Continuation-in-part of Ser. No. 5,061, Jan. 15, 1993, abandoned.

[51] Int. Cl.$^6$ .............................. C12Q 1/68; C12P 19/34; C07H 21/04; C12N 15/00
[52] U.S. Cl. ........................... 435/91.1; 435/6; 435/91.2; 435/810; 536/23.1; 536/24.3; 536/24.33; 536/25.3; 536/25.32; 935/76; 935/77; 935/78
[58] Field of Search ........................... 435/6, 91.1, 91.2, 435/810, 183; 536/24.33, 25.3, 25.32, 23.1, 24.3; 935/1, 8, 16, 76, 77, 78

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |

FOREIGN PATENT DOCUMENTS

| | | |
|---|---|---|
| 329822 | 8/1989 | European Pat. Off. . |
| WO88/10315 | 12/1988 | WIPO . |
| WO89/06700 | 7/1989 | WIPO . |
| WO90/03444 | 4/1990 | WIPO . |

OTHER PUBLICATIONS

Ott, J., et al., "Protection of Oligonucleotide Primers Against Degradation By DNA Polymerase I," *Biochemistry* vol. 26, No. 25, pp. 8237–8241 (1987).
Sayers, J. R., et al., "5'–3' Exonucleases In Phosphorothioate–Based Oligonucleotide Mutagenesis," *Nucleic Acids Res.*, vol. 16, No. 3, pp. 791–802 (1988).
Kunkel, T. A., "The Efficiency of Oligonucleotide–Directed Mutagenesis," In Nucleic Acids and Molecular Biology (F. Eckstein and D. M. J. Lilley (eds.)), Springer Verlag Berlin Heidelberg, 2:124–135 (1988).
Nakamaye, K. L. et al., "Inhibition of Restriction Endonuclease Nci I Cleavage by Phosphorothioate Groups and Its Application to Oligonucleotide–Directed Mutagenesis," *Nucl. Acids Res.*, 14(24):9679–9698 (1986).
Taylor, J. W. et al., "The Use of Phosphorothioate–Modified DNA in Restriction Enzyme Reactions to Prepare Nicked DNA," *Nucl. Acids Res.*, 13(4):8749–8763 (1985).
Taylor, J. W. et al., "The Rapid Generation of Oligonucleotide–Directed Mutations At High Frequency Using Phosphorothioate–Modified DNA," *Nucl. Acids. Res.*, 13(24):8765–8785 (1985).
Gupta, A. P., et al., "The Effect of the 3'–5' Thiophosphate Linkage On the Exonuclease Activities of T4 Polymerase and Klenow Fragment," *Nucl. Acids. Res.*, 12(14):5897–5911 (1984).

Putney, S. D., et al., "A DNA Fragment with an alpha–Phosphorothioate Nucleotide at One End is Asymmetrically blocked from Digestion by Exonuclease III and Can Be Replicated In Vivo," *Proc. Natl. Acad. Sci. U.S.A.*, 78(12):7350–7354 (1981).
Zon, G., et al., "Phosphorothioate Oligonucleotides: Chemistry, Purification, Analysis, Scale–Up and Future Directions," *Anti–Cancer Drug Design* 6:539–568 (1991).
Eckstein, F., et al., "Synthesis and Properties of Disterioisomers of Adenosine 5'–(O–1–Thiophosphate) and Adenosine 5'–(O–2–Thiotriphosphate)," *Biochemistry* 15(8):1685–1691).
Ludwig, et al., "Rapid and Efficient Synthesis of Nucleoside 5'–O–(1–Thiotriphosphates), 5'–Triphosphates and 2',3'–Cyclophosphorothioates Using 2–Chloro–4H–1,3, 2–benzodioxaphosphorin–4–one," *J. Org. Chem.*, 54:631–635 (1989).
Kim, S–G, et al., "Phosphorothioate Analogues of Oligodeoxyribonucleotide: Synthesis and Activity as Inhibitors of Replication of Human Immunodeficiency Virus," *Biochem. Biophysical Res. Comm.*, 179(3):1614–1619 (1991).
Vu, H., et al., "Internucleotide Phosphite Sufurization with Tetraethylthiuram Disulfide. Phosphorothioate Oligonucleotide Synthesis Via Phosphoramidite Chemistry," *Tetrahedron Letters* 32(26):3005–3008 (1991).
Goodchild, J., "Conjugates of Oligonucleotides and Modified Oligonucleotides: A Review of Their Synthesis and Properties" *Bioconjugate Chemistry* 1(3):165–187 (1990).
Labeit, S., et al., "Laboratory Methods: A New Method of DNA Sequencing Using Deoxynucleoside alpha–Thiotriphosphates," *DNA* 5(2):173–177 (1986).
Gish, G., et al., "DNA and RNA Sequencing Using Phosphorthioate Chemistry," *Nucl. Acids Res. Sym. Series* 18:253–256 (1987).
Wu, D., et al., "The Ligation Amplification Reaction (LAR)–Amplification of Specific DNA Sequences Using Sequential Rounds of Template–Dependent Ligation" *Genomics* 4:560–569 (1989).
Gyllensten, U. B., et al., "Generation of Single–Stranded DNA by the Polymerase Chain Reaction and Its Application to Direct Sequencing of the HLA–DQA Locus" *Proc. Natl. Acad. Sci.*, U.S.A., 85:7652–7656 (1988).
Mihovilovic, M., et al., "An Efficient Method for Sequencing PCR Amlified DNA" *BioTchniques* 7(1):14–16 (1989).
Higuchi, R. G., et al., "Production of Single–Stranded DNA Templates by Exonuclease Digestion Following the Polymerase Chain Reaction" *Nucleic Acids Res.*, 17(14):5865 (1989).

(List continued on next page.)

*Primary Examiner*—W. Gary Jones
*Assistant Examiner*—Bradley L. Sisson
*Attorney, Agent, or Firm*—Howrey & Simon

[57] ABSTRACT

A method for generating single-stranded nucleic acid molecules. The molecules contain nuclease resistant modified nucleotides, such that they are resistant to 5'→3' exonucleases.

14 Claims, No Drawings

OTHER PUBLICATIONS

Kwoh, D. Y., et al., "Transcription–Based Amplification System and Detection of Amplified Human Immuodeficiency Virus Type 1 with a Bead–Based Sandwich Hybridization Format" *Proc. Natl. Acad. Sci. U.S.A.*, 86:1173–1177 (1989).

Ohara, O., et al., "One–Sided Polymerase Chain Reaction: The Amplification of cDNA," *Proc. Natl. Acad. Sci. U.S.A.*, 86:5673–5677 (1989).

Frohman, M. A., et al., "Rapid Production of Full–Length cDNAs From Rare Transcripts: Amplification Using a Single Gene–Specific Oligonucleotide Primer," *Proc. Natl. Acad. Sci. U.S.A.*, 85:8998–9002 (1988).

Loh, E. Y., et al., "Polymerase Chain Reaction with Single-–Sided Specificity: Analysis of T Cell Receptor Gama–Chain," *Science* 243:217–243 (1989).

Frohman, M. A., et al., "RACE: Rapid Amplification of cDNA Ends," In PCR Protocols: A Guide to Methods and Applications, Academic Press, Inc., pp. 28–38 (1990).

Saiki, R. K., et al., "A Novel Method for the Detection of Polymorphic Restriction Sites by Cleavage of Oligonucleotide Probes: Application to Sickle–Cell Anemia," *Biotechnology* 3:1008–1012 (1985).

Nickerson, D. A., et al., "Automated DNA Diagnostics Using an ELISA–Based Oligonucleotide Ligation Assay," *Proc. Natl. Acad. Sci. U.S.A.*, 87:8923–8927 (1990).

Mullis, K. et al., "Specific Enzymatic Amplification of DNA In Vitro: The Polymerase Chain Reaction," *Cold Spring harbor Symposia on Quantitative Biology* 51:263–273 (1986).

Mullis, K., et al., "Specific Synthesis of DNA In Vitro Via a Polymerase–Catalyzed Chain Reaction," *Methods Enzymol.*, 155:355–350 (1987).

Walker, G. T., et al., "Isothermal in vitro Amplification of DNA by a Restriction Enzyme/DNA Polymerase System" *Proc. Natl. Acad. Sci. U.S.A.*, 89:392–396 (1992).

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:1:

CTCCACCCTT ATGAACTCAT TGAAT 25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:2:

TGTGTGTGCT ATAAATGCCA CTAAC 25

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:3:

CCGCGTGGTG CCTGGTGCCC TTTTTGGGCA CCAGGCACCA CGCGG      45

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:4:

CCGCGTGGTG CCTGGTGCCC TTTTTGGGCA CCAGGCACCA CGCGG      45

( 2 ) INFORMATION FOR SEQ ID NO:5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:5:

CCGCGTGGTG CCTGGTGCCC TTTTTGGGCA CCAGGCACCA CGCGG      45

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:6:

AGCCTCAGAC CGCGTGGTGC CTGGT      25

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:7:

CCAAGGAGC TGGGTCTGAA ACAAA 25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:8:

ATGGCTTCCC ACCCTACCCA TCCCG 25

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Equus caballus ( x i ) SEQUENCE DESCRIPTION: SEQ ID NO:9:

TGTTCTGGGA AAGACCACAT TATTT 25

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:10:

ATGCTCCCAG GTGATTCCAG TGTGC 25

( 2 ) INFORMATION FOR SEQ ID NO:11:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:11:

GGTGCTGTGC GAGGTACACT TGACTG                              26

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:12:

AGAAACACAA GGCCCAAGAA CAGGA                               25

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:13:

GGATCCAGAT GAACAACCAG ATGAA                                25

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:14:

CTGCAGCCCA CTGGGCCTTC TTTGT    25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:15:

CCTTTGTGTA GAGTAGTTCA AGGAC    25

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:16:

ATAATACAGA AGTTCTGAGA GGCTA    25

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Equus caballus ( x i ) SEQUENCE DESCRIPTION: SEQ ID NO:17:

GGATCCAGGT CTGCTTCTGC TTCCC    25

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Equus caballus ( x i ) SEQUENCE DESCRIPTION: SEQ ID NO:18:

AAGAGAAAGA GTTTTGCCTC AATCC     25

METHOD FOR GENERATING SINGLE-STRANDED DNA MOLECULES

CROSS-REFERENCE TO RELATED APPLICATIONS

This application is a continuation-in-part of U.S. patent application Ser. No. 08/005,061, filed Jan. 15, 1993, and now abandoned, herein incorporated by reference.

FIELD OF THE INVENTION

The invention relates to a method for generating single-stranded DNA molecules. More specifically, it relates to the use of modified nucleotides and a 5'→3' exonuclease to produce single-stranded nucleic acid molecules following primer-mediated extension.

BACKGROUND OF THE INVENTION

The analysis of the structure, organization and sequence of nucleic acid molecules is of profound importance to the prediction, diagnosis and treatment of human and animal disease, in forensics, in epidemiology and public health, and in the elucidation of the factors that control gene expression and development.

Three areas of particular importance involve the development of nucleic acid molecules that are capable of hybridizing to a desired sequence, the generation of nucleic acid molecules that are single-stranded, and the determination of the nucleotide sequence of a nucleic acid molecule.

I. Nucleic Acid Hybridization

The capacity of a nucleic acid "probe" molecule to hybridize (i.e. base pair) to a complementary nucleic acid "target" molecule forms the cornerstone for a wide array of diagnostic and therapeutic procedures.

Hybridization is used to detect and identify causal agents of infectious disease, to provide information on paternity and lineage, to predict the likelihood that an individual will suffer from a genetic disease, or to identify tissue samples. The diagnostic value of such procedures hinges on their sensitivity. Sensitivity can be increased through the use of probes that are detectably labelled. The most common label involves the use of radioisotopic labels (Falkow et al. (U.S. Pat. No. 4,358,535); Berninger (U.S. Pat. No. 4,446,237). Methods of labeling and performing such hybridization reactions are disclosed by, for example, Sambrook, J. et al. (In: *Molecular Cloning: A Laboratory Manual*, Cold Spring Harbor Laboratory Press, Cold Spring Harbor, N.Y. (1989)), and Haymes, B. D., et al. (In: *Nucleic Acid Hybridization, A Practical Approach*, IRL Press, Washington, D.C. (1985)) which references are included herein by reference.

The sensitivity of nucleic acid hybridization detection assays may also be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Fluorescent labels (Albarella et al., EP 144914), chemical labels (Sheldon III et al., U.S. Pat. No. 4,582,789; Albarella et al,, U.S. Pat. No. 4,563,417), modified bases (Miyoshi et al., EP 119448), etc. have also been used in an effort to improve the efficiency with which hybridization can be observed.

Hybridization assays employing synthetically or enzymatically made single-stranded nucleic acid probes can be performed in solution (Berk, A. J. et al., *Cell* 12:721–732 (1977); Hood, L. E. et al., In: *Molecular Biology of Eukaryotic Cells: A Problems Approach*, Menlow Park, Calif.: Benjamin-Cummings (1975); Wetmer, J. G., *Ann. Rev. Biophys. Bioeng.* 5:337–361 (1976); Itakura, K. et al., *Ann. Rev. Biochem.* 53:323–356 (1984)) or in conjunction with gel electrophoresis or nucleic acid-binding membrane blotting methods. Such methods also allow the detection of nucleic acid molecules with sequences that are complementary to all or part of the probe (Alwine, J. C. et al., *Proc. Natl. Acad. Sci. (U.S.A.)* 74:5350–5354 (1977); Southern, E. M., *J. Molec. Biol.* 98:503–517 (1975)); Berk, A. J. et al., *Cell* 12:721–732 (1977); Itakura, K. et al., *Ann. Rev. Biochem.* 53:323–356 (1984); Ruddle, F. H., *Nature* 294:115–119 (1981); White, R. et al., *Sci. Amer.* 258:40–48 (1988); McGinnis, W. et al., *Cell* 37:403–408 (1984)). Single-stranded nucleic acid probes can also be used in situ to locate specific nucleic acid sequences in a method termed "in situ hybridization" (Abelson, J. et al., *Science* 209:1317–1438 (1980); Gilbert, W. et al., *Sci. Amer.* 242:74–94 (1980)).

Hybridization assays may also be performed using affinity chromatography methods. In this method, one single-stranded nucleic acid molecule, usually an oligonucleotide, is immobilized to a solid support matrix and used as a probe to hybridize a second complementary single-stranded nucleic acid molecule. Efficient detection or recovery of a single desired nucleic molecule is enhanced when the two complementary single-stranded sequences are present in non-limiting concentrations and each are in substantially pure form. For example, single-stranded oligonucleotides of high purity have been isolated from solution by affinity chromatography using immobilized (i.e. bound to solid support matrix) oligonucleotides complementary to the oligomers in solution, as discussed for example, in Gilham et al. (*J. Amer. Chem. Soc.* 86:4982 (1964)) and Kremsky et al. (*Nucl. Acids Res.* 15:3131–3139 (1987)).

The capacity of DNA molecules to hybridize to complementary mRNA molecules, and thereby attenuate the translation of specific proteins forms one basis for the therapeutic application of hybridization technology. Such "antisense" technology has significant potential in anti-viral and anti-cancer therapy. Antisense technology is discussed in European Patent Application Publication Nos. 263,740; 335,451; and 329,882, and in PCT Publication No. WO90/00624, all of which references are incorporated herein by reference.

Hybridization technology is also exploited to aid in the recovery of RNA. In the case of eukaryotic mRNA, this has been accomplished using affinity matrix chromatography columns having polydeoxythymidine oligonucleotides bound to a solid support matrix comprised of cellulose (i.e. Oligo (dT)-cellulose columns). Such oligonucleotides are capable of hybridizing to the polyadenine mRNA "tails" normally found on the 3' end of all eukaryotic mRNA molecules (Gilham, P. T., *J. Amer. Chem. Soc.* 86:4982 (1971)). Such methods of isolating single-stranded nucleic acid molecules require large quantities of starting material.

II. The Amplification of Nucleic Acid Molecules

The ability to detect the presence of a desired target nucleic acid molecule in a sample is often limited by the concentration of the molecule in either its double-stranded and single-stranded forms. In many such situations, the concentration of the target can be amplified through the use of either in vivo or in vitro based amplification systems.

In vivo based amplification systems include amplification of a target nucleotide molecule through its propagation (i.e. replication and amplification) in cloning or expression vectors. Cloning and expression vectors are disclosed, for example, in Sambrook, J. et al. (In: *Molecular Cloning: A Laboratory Manual*, Cold Spring Harbor Laboratory Press, Cold Spring Harbor, N.Y. (1989)).

Commonly employed in vitro based amplification systems include enzymatic methods using DNA dependent or RNA dependent DNA or RNA polymerases. The most widely used method of nucleic acid amplification, the "polymerase chain reaction" ("PCR"), involves template-dependent extension using thermally stable DNA polymerase (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference. PCR achieves the amplification of a specific nucleic acid sequence using two oligonucleotide primers complementary to regions of the sequence to be amplified. Extension products incorporating the primers then become templates for subsequent replication steps. Reviews of the polymerase chain reaction are provided by Mullis, K. B. (*Cold Spring Harbor Symp. Quant. Biol.* 51:263–273 (1986)); Saiki, R. K. et al. (*Bio/Technology* 3:1008–1012 (1985)); and Mullis, K. B. et al. (*Meth. Enzymol.* 155:335–350 (1987), which references are incorporated herein by reference).

Other nucleic acid amplification procedures include transcription-based amplification systems (Kwoh D et al., *Proc. Natl. Acad. Sci. (U.S.A.)* 86:1173 (1989); Gingeras T. R. et al., PCT appl. WO 88/10315 (priority: U.S. patent application Ser. Nos. 064,141 and 202,978); Miller, H. I. et al., PCT appl. WO 89/06700 (priority: U.S. patent application Ser. No. 146,462); Davey, C. et al. (European Patent Application Publication no. 329,822)) and ligation-based amplification systems (Wu, D. Y. et al., *Genomics* 4:560 (1989)).

Although amplification technologies can be used to achieve the rapid and extensive amplification of a polynucleotide molecule, such methods generally result in the production of double-stranded DNA. Thus, the methods, in general fail to provide a selective means for amplifying and isolating a single-strand of a double-stranded target molecule.

Single-stranded DNA molecules may be produced using the single-stranded DNA bacteriophage M13 (Messing, J. et al., *Meth. Enzymol.* 101:20 (1983); see also, Sambrook, J. et al. (In: *Molecular Cloning: A Laboratory Manual*, Cold Spring Harbor Laboratory Press, Cold Spring Harbor, N.Y. (1989)). Use of M13 to produce single-stranded DNA, however, requires cloning and other time consuming manipulations, and thus M13 is primarily used for DNA sequencing. In general, the method entails cloning a target DNA molecule into the single-stranded DNA chain of M13. Once introduced into a host bacterium, the recombinant M13 vector directs the formation and extrusion of bacteriophage particles that contain single-stranded DNA.

There are several major disadvantages in using M13 to produce single-stranded DNA molecules. First, the method requires the cloning of the target DNA, and the ultimate isolation and purification of the mature bacteriophage particles. Hence, the method is quite time consuming. More significantly, the isolated target DNA is unavoidably attached to the M13 viral DNA sequences. A further disadvantage to the M13 system is due to the instability of DNA target molecules larger than 1000 nucleotides which often results in loss of the desired recombinant M13 phage. For the forgoing reasons, M13 is not used to generate single-stranded DNA for most applications other than DNA sequencing.

Several methods are currently used for generating single-stranded DNA molecules. Gyllensten, U. et al. (*Proc. Natl. Acad. Sci. (U.S.A.)* 85:7652–7656 (1988) and Mihovilovic, M. et al. (*BioTechniques* 7:14 (1989)) describe a method involving a modification of the standard "PCR" method which is normally used for amplifying double-stranded DNA molecules. This modified PCR procedure, termed "asymmetric PCR," employs amplification primers present in different molar concentrations. When asymmetric primer concentrations are used in the "asymmetric PCR" technique, the primer in limiting concentration becomes exhausted after the first 10 to 15 amplification cycles. Continued cycling generates single-stranded DNA originating from the non-limiting primer.

There are, unfortunately, several disadvantages to employing "asymmetric PCR" to obtain single-stranded DNA. Single-stranded DNA amplification only occurs linearly with cycle number in contrast to exponential DNA amplification when using the standard PCR method. Additionally, to optimize the yield of single-stranded product, it is often necessary to carry out several separate amplification reactions that contain varying concentrations and ratios of the priming oligonucleotides. The advantages to generating single-stranded DNA in combination with an exponentially producing amplification reaction, such as the standard non-asymmetric PCR, are thus apparent.

Higuchi, R. G. et al. (*Nucl. Acids Res*, 17:5865 (1985)) exemplifies an additional method currently used for generating single-stranded amplification products. The method entails phosphorylating the 5' terminus of one strand of a double-stranded amplification product, and then permitting a 5'→3' exonuclease (such as λ exonuclease) to preferentially degrade the phosphorylated strand. The method thus has several drawbacks. The efficiency of the method depends both on the extent and specificity of the phosphorylation reaction, and on the degree of preference exhibited by the exonuclease.

5'→3' exonucleases have been used to prepare single-stranded DNA fragments from full-length double-stranded DNA molecules. When such a full-length molecule is incubated in the presence of a 5'→3' exonuclease, degradation occurs from the 5' terminus of each strand. The degradation of the first strand continues until the exonuclease acting on that strand reaches the region in which the second strand has been degraded by the exonuclease acting on that strand. Thus, the method produces two "half-length," non-complementary molecules from a full-length duplex DNA molecule.

Additionally, other methods have exploited the nuclease resistant properties of phosphorothioate derivatives for generating single-stranded DNA molecules. Benkovic et al. (U.S. Pat. No. 4,521,509; Jun. 4, 1985)) used the restriction endonuclease and the 3'→5' exonuclease resistant properties of phosphorothioate-containing nucleic acid sequences to generate single-stranded DNA molecules. This method employs the use of a restriction endonuclease to form a double-stranded molecule having a single recessed 3' hydroxyl terminus. Phosphorothioate nucleotides are used to modify this terminus, thereby producing a strand that is resistant to exonuclease attack, which permits the generation of a single-stranded product. This method is limiting since the target DNA sequence must contain two desired restriction endonuclease sites: the first must create a recessed 3'-OH terminus, and be at one end of the target molecule and the second must create a recessed 5' terminus, and be at the second end. A further limitation to this method is that production of a desired single-stranded DNA product requires a high concentration of target double-stranded DNA molecules.

Sayers, J. R. et al. (*Nucl. Acids Res.* 16:791–802 (1988)) exemplifies a method that uses the restriction endonuclease-resistant properties of phosphorothioate-containing DNA to produce single-stranded DNA. In the method, a primer is permitted to hybridize to a circular target molecule. Primer extension then occurs in the presence of phosphorothioate nucleotides, such that the nucleotide derivatives are incorporated into the extension product. The termini of the extension product are then ligated, to form a double-stranded circular molecule. The presence of the phosphorothioate residues in the circularized extension product renders that strand resistant to restriction endonucleases. Thus, upon incubation with such endonucleases, the target strand is cleaved. Such cleavage generates termini that can then be attacked by exonucleases. Significantly, the exonuclease resistance of the phosphorothioate-containing strand cannot be evaluated, since that strand, being circular, is not a substrate for an exonuclease.

Phosphorothioate-containing oligonucleotides have been found to protect oligonucleotide primers from degradation by the 5'→3' "mismatch" exonuclease activity of polymerase I (Ott, J. et al., *Biochem* 26:8237–8241 (1987). The method of Ott et al., since it employs a polymerase, is incapable of producing single-stranded DNA.

Although the method is suitable for site-directed mutagenesis, it is limited by its dependency on using the cumbersome and limited bacteriophage M13 system described above. Additionally, the Sayers et al. method requires the presence of a restriction endonuclease cleavage site in the target molecule.

In sum, the ability to manipulate and exploit nucleic acid molecules often requires the isolation of a single-stranded molecular species. Present methods of nucleic acid amplification typically lead to the formation of double-stranded species, and thus require additional processing steps in order to obtain purified preparations of single-stranded molecules.

III. The Sequencing of Nucleic Acid Molecules

Initial attempts to determine the sequence of a DNA molecule employed extensions of techniques that had been developed to permit the sequencing of RNA molecules (Sanger, F., *J. Molec. Biol.* 13:373 (1965); Brownlee, G. G. et al., *J. Molec. Biol,* 34:379 (1968)). Such early methods involved the specific cleavage of DNA into smaller fragments by (1) enzymatic digestion (Robertson, H. D. et al., *Nature New Biol.* 241:38 (1973); Ziff, E. B. et al., *Nature New Biol.* 241:34 (1973)); (2) nearest neighbor analysis (Wu, R. et al., *J. Molec. Biol,* 57:491 (1971)), and (3) the "Wanderings Spot" method (Sanger, F., *Proc. Natl. Acad. Sci. (U.S.A.)* 70:1209 (1973)).

More recent advances have led to the development of two highly utilized methods for elucidating the sequence of a DNA molecule: the "Dideoxy-Mediated Chain Termination Method," also known as the "Sanger Method" (Sanger, F. et al., *J. Molec. Biol,* 94:441 (1975)) and the "Maxam-Gilbert Chemical Degradation Method" (Maxam, A. M. et al., *Proc. Natl. Acad. Sci. (U.S.A.)* 74:560 (1977), both references herein incorporated by reference). Methods for sequencing DNA using either the dideoxy-mediated method or the Maxam-Gilbert method are widely known to those of ordinary skill in the art. Such methods are, for example, disclosed in Maniatis, T., et al., *Molecular Cloning, a Laboratory Manual, 2nd Edition,* Cold Spring Harbor Press, Cold Spring Harbor, N.Y. (1989), and in Zyskind, J. W. et al., *Recombinant DNA Laboratory Manual,* Academic Press, Inc., New York (1988), both herein incorporated by reference.

In the dideoxy-mediated method, the sequence of a target molecule is determined using four separate primer extension reactions, each of which are conducted using a polymerase, an oligonucleotide primer, and the four nucleotide triphosphates needed to polymerize DNA. Each of the reactions is carried out in the additional presence of a 2', 3' dideoxy derivative of either an A, T, C, or G nucleoside triphosphate. Such derivatives differ from conventional nucleotide triphosphates in that they lack a hydroxyl residue at the 3' position of deoxyribose. Thus, although they can be incorporated into the newly synthesized primer extension, such incorporation results in the termination of the extension reaction. The net result of each of the four reactions is the production of a set of nested oligonucleotides each of which is terminated by the particular dideoxy derivative used in the reaction. Such reaction products can be readily analyzed to yield the sequence of the target molecule.

The Maxam-Gilbert method of DNA sequencing is a degradative method. In this procedure, a fragment of DNA is labeled at one end and partially cleaved in four separate chemical reactions, each of which is specific for cleaving the DNA molecule at a particular base (G or C) at a particular type of base (A/G, C/T, or A>C). As in the above-described dideoxy method, the effect of such reactions is to create a set of nested molecules whose lengths are determined by the locations of a particular base along the length of the DNA molecule being sequenced. The nested reaction products can be analyzed to yield the sequence of the target molecule.

In general, multiple sets of nested oligonucleotides must be evaluated in order to determine the sequence of the target molecule, however, various modifications, such as the use of multiple, distinguishable labels has led to the development of "multiplexing" methods that are capable of yielding increased sequence data (Church, G. M. et al., *Science* 240:185–188 (1988); Church, G. M. et al., U.S. Pat. No. 4,942,124; Tabor, et al., U.S. Pat. No. 4,962,020; Prober, J. M. et al., *Science* 238:336–340 (1987)).

Other "multiplexing" sequencing method such as described by Macevicz, S. C., (U.S. Pat. No. 5,002,867) are directed to methods for determining the nucleotide sequence of a DNA or an RNA molecule using multiple mixed oligonucleotide probes. Sequence information is obtained by carrying out a series of hybridizations whose results provide for each probe the number of times the complement of the probe's sequence occurs in the RNA or DNA whose sequence is to be determined. The nucleotide sequence of the RNA or DNA is reconstructed from this information and from a knowledge of the probes' sequences. The nucleic acid whose sequence is to be determined is referred to herein as the target sequence.

The double-stranded structure of DNA complicates the sequence analysis process. Because the two strands of DNA are symmetrical and chemically identical, a sequence analysis that is conducted using both strands of a DNA molecule will yield two indistinguishable sets of sequence data. Thus, it is highly desirable to perform sequence analysis using preparations of DNA that contain only one of the two strands. Unfortunately, because the DNA strands are chemically indistinguishable, it is in general quite difficult to obtain DNA preparations that contain only one strand. The dideoxy sequencing method attempts to avoid this problem by employing either a DNA source that is single-stranded (such as a bacteriophage M13 or phagemid vector (Sambrook, J. et al., *Molecular Cloning, a Laboratory Manual, 2nd Edition*, Cold Spring Harbor Press, Cold Spring Harbor, N.Y. (1989), herein incorporated by reference)) or a primer that is capable of binding to only one strand of a target molecule. As will be appreciated, since the sequence of the target molecule is unknown, there can be no a priori assurance that a particular primer will not hybridize to both DNA strands. In the case of the Maxam-Gilbert method, it is in general necessary to label both strands of the target molecule, and then to selectively remove the label from one of the strands. These manipulations complicate the determinations of nucleic acid sequence.

In view of the deficiencies of the above-described methods for preparing single-stranded DNA, and in view of the importance of such methods to a variety of molecular biology and medical procedures, a method that would preferentially produce a single strand of a desired target molecule, and which could be used in conjunction with nucleic acid amplification procedures would be extremely desirable. The present invention provides such a method.

SUMMARY OF THE INVENTION

The present invention provides a method for generating single-stranded DNA molecules following a primer-mediated o extension or amplification reaction. Such molecules are useful as hybridization probes and in nucleic acid sequencing.

In detail, the invention provides a method for generating a desired single-stranded nucleic acid molecule, substantially free of any nucleic acid molecule of complementary sequence, said method comprising the steps:

A) incubating a preselected nucleic acid molecule in the presence of a primer molecule; wherein said primer molecule is capable of hybridizing to said preselected molecule, and wherein said primer molecule contains a region that is resistant to a 5'→3' exonuclease;

B) permitting template-dependent extension of said primer to thereby form said desired nucleic acid molecule; and C) adding to said incubation a 5'→3' exonuclease, under conditions sufficient to eliminate said preselected molecule, and to thereby generate said desired single-stranded molecule substantially free of any nucleic acid molecule of complementary sequence.

The invention additionally includes the embodiment of the above method wherein in step B, after forming the desired nucleic acid molecule, the molecule is incubated in the presence of a second primer molecule capable of hybridizing thereto, and of being extended in a template-dependent manner to thereby form a nucleic acid molecule having a sequence substantially complementary to that of the desired molecule.

The invention also provides a composition of matter comprising a target nucleic acid molecule, hybridized to a primer molecule having a length of from about 10 to about 30 nucleotides and containing a nucleotide that confers 5'→3' exonuclease resistance to the primer molecule.

The invention particularly concerns the embodiment of the above methods wherein the exonuclease resistance of the region that is resistant to a 5'→3' exonuclease is caused by a plurality of phosphorothioate nucleotide derivatives.

The invention also provides a method of determining the identity of a nucleotide base at a specific position in a nucleic acid of interest, which comprises:

A) treating a sample containing the nucleic acid of interest, if the nucleic acid is double-stranded, so as to obtain unpaired nucleotide bases spanning the specific position, or directly employing step (B) if the nucleic acid of interest is single-stranded, wherein the nucleic acid of interest contains a sufficient number of 5'→3' exonuclease resistant nucleotide derivatives to confer 5'→3' exonuclease resistance to a region of said nucleic acid of interest;

B) contacting the sample from step (A), under hybridizing conditions, with an oligonucleotide primer which is capable of hybridizing with a stretch of nucleotide bases present in the nucleic acid of interest immediately adjacent to the nucleotide base to be identified, so as to form a duplex between the primer and the nucleic acid of interest such that the nucleotide base to be identified is the first unpaired base in the template immediately downstream of the 3' terminus of the primer in the duplex; and C) contacting the duplex from step (B), in the substantial absence of dATP, dCTP, dGTP or dTTP, with at least two different nucleotide triphosphate derivatives, the derivatives including a derivative complimentary to the first unpaired base, and being terminators of a nucleic acid template-dependent, primer extension reaction; wherein at least one of the terminators is labeled with a detectable marker; and wherein the contacting is under conditions sufficient to permit base pairing of the complementary terminator derivative with the first unpaired base;

D) permitting occurrence of a template-dependent primer extension reaction sufficient to incorporate the complementary terminator derivative onto the 3' terminus of the primer;

E) determining the identity of the incorporated derivative, and thereby determining the identity of the nucleotide base at the specific position in the nucleic acid of interest.

The invention additionally includes the embodiments of the above method wherein in step (C), the duplex from step (B) is contacted with four terminators, wherein only one of the terminators has a detectable marker, and wherein the step (C) is performed four times, each time with a different one of the terminators being labelled; or wherein in step (C), the duplex from step (B) is contacted with four labeled terminators, each with a different detectable label.

The invention also includes a method for detecting a desired exonuclease resistant amplification product of a polymerase chain reaction which comprises:

A) conducting a polymerase chain reaction with two primer molecules, wherein one of the primer molecules contains a sufficient number of phosphorothioate nucleotide derivatives (most preferably, about 4) at that primer's 5' terminus to render the terminus resistant to a 5'→3' exonuclease; the reaction being sufficient to form double-stranded amplification products;

B) subsequently treating the amplification products with a 5'→3' exonuclease under conditions to degrade oligonucleotides that lack a sufficient number of phosphorothioate bonds to render the oligonucleotides resistant to the exonuclease C) detecting the desired amplification product of the polymerase chain reaction by permitting the product to hybridize to a complementary oligonucleotide bound to a solid support.

The invention also includes a method for minimizing cross contamination between polymerase chain reactions which comprises conducting a polymerase chain reaction wherein at least one of the primer molecules of the reaction contains a sufficient number of phosphorothioate nucleotide derivatives (i.e. about 4) at that primer's 3' terminus to render the terminus resistant to a 5'→3' exonuclease; and wherein, subsequent to conducting the polymerase chain reaction, amplification products of the reaction are incubated in the presence of said 5'→3' exonuclease under conditions sufficient to permit the degradation of oligonucleotide regions of unused primers and of amplification products that lack the sufficient number of phosphorothioate bonds; the degradation rendering the unused primer and the amplification products substantially incapable of serving as substrates in an additional polymerase chain reaction, and thereby minimizing cross contamination between polymerase chain reactions.

The invention also includes a kit, being specially adapted to contain in close compartmentalization a first container which contains a first primer, the first primer containing a phosphorothioate nucleotide derivative; and a second container which contains a second primer lacking any phosphorothioate nucleotide derivatives, such that the two primers can be used to amplify a predetermined gene sequence.

DESCRIPTION OF THE PREFERRED EMBODIMENTS

I. Introduction

The present invention provides a method for generating single-stranded DNA molecules, especially following the preparation of double-stranded nucleic acid molecules by an in vitro amplification procedure, such as PCR. The method employs nuclease resistant nucleotides derivatives, and incorporates, by chemical synthesis or enzymatic means, these derivatives into primer molecules in place of naturally occurring nucleotides.

The molecules that can be generated through the use of the present method can have a length ranging from a few nucleotides to several kilobases. The "desired" molecules of the invention are said to have a sequence that is "complementary," or substantially complementary to the sequence of a "target" strand of a nucleic acid molecule.

As used herein, two molecules are said to be complementary if they can hybridize to one another with sufficient stability to permit them to remain annealed to one another under at least conventional "low-stringency" conditions (see, Sambrook, J. et al., *Molecular Cloning, a Laboratory Manual, 2nd Edition*, Cold Spring Harbor Press, Cold Spring Harbor, N.Y. (1989), herein incorporated by reference).

The target molecule may be either DNA, cDNA or RNA; it may be either single-stranded or double-stranded. Where the "target" molecule is double-stranded, the invention distinguishes these strands as being either a "target" strand or a "complement" strand (whose sequence is complementary to that of the target sequence). If the target molecule is double-stranded, the method of the present invention can be used to generate either of such strands.

Significantly, the method of the present invention permits one to generate single-stranded molecules that have the same length as the target molecule. The capacity to form full-length molecules (rather than molecules comprising only fragments of full-length molecules) greatly simplifies sequencing analysis, and facilitates the preparation of hybridization probes.

The present invention is capable of generating single-stranded molecules regardless of the nature, origin or sequence of the target molecule. Thus, the present invention can be used to generate single-stranded molecules that have a naturally occurring sequences, such as a sequence present in a virus (e.g. rhinovirus, hepatitis virus, herpes virus, HIV, etc.), a bacterium (e.g. Escherichia, Clostridium, Mycobacterium, Neisseria, Mycoplasma, Vibrio, Chlamydia, Rickettsia, etc.), a yeast, a fungus, or other lower eukaryote. In particular, the present invention can be used to generate single-stranded molecules that have sequence present in a plant cell, or an animal cell (especially a mammalian cell, such as from a horse, cow, dog, cat or human). The present invention can also be used to generate single-stranded molecules that are purely or partially synthetic (i.e. non-naturally occurring).

Significantly, the method of the invention permits the generated single-stranded molecules to be obtained "substantially free" of other sequences with which it is naturally associated. As used herein, the term "substantially free" denotes the reduction or elimination of at least one other sequence which is naturally associated with the obtained sequence or its complement.

The present invention accomplishes the generation of such single-stranded molecules through the use and extension of "primer" molecules that contain exonuclease resistant nucleotide derivatives. Examples of such modified nucleotide derivatives are disclosed by Zon, G. et al. (*Anti-Cancer Drug Design* 6:539–568 (1991)) and Goodchild, J. et al. (*Bionconjugate Chem.* 1:613–629 (1990)), both of which references are incorporated herein by reference. In general, suitable nucleotide derivatives include derivatives in which one or two of the non-bridging oxygens of the phosphate moiety of a nucleotide has been replaced with a sulfur-containing group (especially a phosphothioate), an alkyl group (especially a methyl or ethyl alkyl group), a nitrogen-containing group (especially an amine), and/or a selenium-containing group, etc. For the purpose of the present invention, phosphorothioate nucleotide derivatives are the most preferable derivatives. A phosphorothioate nucleotide derivative (e.g. a nucleoside 5'-O-1-thiotriphosphate) contains a non-bridging (i.e. monocoordinate) sulfur in place of the oxygen atom of the orthophosphate moiety. As will be appreciated, the introduction of the sulfur permits two stereoisomers to form. Such a racemic mixture is suitable for the purposes of the present invention.

Importantly, the selected nucleotide derivative must be suitable for in vitro primer-mediated extension and provide nuclease resistance to the region of the nucleic acid molecule in which it is incorporated. In the most preferred embodiment, it must confer resistance to exonucleases that attack double-stranded from the 5' end ("5'→3' exonucleases"). Examples of such exonucleases include bacteriophage T7 gene 6 exonuclease ("T7 exonuclease") and the bacteriophage lambda exonuclease ("λ exonuclease"). Both T7 exonuclease and λ exonuclease are inhibited to a significant degree by the presence of phosphorothioate bonds so as to allow the selective degradation of one of the strands. However, any double-strand specific, 5'→3' exonuclease can be used for this process, provided that its activity is affected by the presence of the bonds of the nuclease resistant nucleotide derivatives. The preferred enzyme when using phosphorothioate derivatives is the T7 gene 6 exonuclease, which shows maximal enzymatic activity in the same buffer used for many DNA dependent polymerase buffers including Taq polymerase. The 5'→3' exonuclease resistant properties of phosphorothioate derivative-containing DNA molecules are discussed, for example, in Kunkel, T. A. (In: *Nucleic Acids and Molecular Biology,* Vol. 2, 124–135 (Eckstein, F. et al., eds.), Springer-Verlag, Berlin, (1988)). The 3'→5' exonuclease resistant properties of phosphorothioate nucleotide containing nucleic acid molecules are disclosed in Putney, S. D. et al. (*Proc. Natl. Acad. Sci. (U.S.A.)* 78:7350–7354 (1981)) and Gupta, A. P. et al. (*Nucl. Acids. Res.,* 12:5897–5911 (1984)).

In addition to being resistant to such exonucleases, nucleic acid molecules that contain phosphorothioate derivatives at restriction endonuclease cleavage recognition sites are resistant to such cleavage. Taylor, J. W. et al. (*Nucl. Acids Res.* 13:8749–8764 (1985)) discusses the endonuclease resistant properties of phosphorothioate nucleotide containing nucleic acid molecules.

The nuclease resistance of phosphorothioate bonds has been utilized in a DNA amplification protocol (Walker, T. G. et al. (*Proc. Natl. Acad. Sci. (U.S.A.)* 89:392–396 (1992)). In the Walker et al. method, phosphorothioate nucleotide derivatives are installed within a restriction endonuclease recognition site in one strand of a double-stranded DNA molecule. The presence of the phosphorothioate nucleotide derivatives protects that strand from cleavage, and thus results in the nicking of the unprotected strand by the restriction endonuclease. Amplification is accomplished by cycling the nicking and polymerization of the strands.

Similarly, this resistance to nuclease attack has been used as the basis for a modified "Sanger" sequencing method (Labeit, S. et al. (*DNA* 5:173–177 (1986)). In the Labeit et al. method, $^{35}$S-labelled phosphorothioate nucleotide derivatives were employed in lieu of the dideoxy nucleotides of the "Sanger" method.

As indicated, other methods (such as asymmetric PCR, etc.) have been used in attempts to generate single-stranded molecules. The methods of the present invention offer the advantage that the double-stranded PCR product is quantitatively converted to a single-stranded product of exactly the same length. Second, the exonuclease used shows optimal enzymatic activity in PCR salts, thus no purification or buffer exchange is required prior to the exonuclease treatment. Finally, the resulting single-stranded molecule is completely resistant to any further degradation by the T7 gene 6 exonuclease.

The term "primer," as used herein, refers to a single-stranded oligonucleotide or a single-stranded polynucleotide that is capable of being extended by the covalent addition of a nucleotide in a "template-dependent" extension reaction. In order to possess such a capability, the primer must have a 3' hydroxyl terminus, and be hybridized to a second nucleic acid molecule (i.e. the "template"). A primer is typically 11 bases or longer; most preferably, a primer is 25 bases, however, primers of shorter or greater length may suffice. "Template-dependent" extension refers to the capacity of a polymerase to mediate the extension of a primer such that the extended sequence is complementary to the sequence of a nucleic acid template. A "polymerase" is an enzyme that is capable of incorporating nucleoside triphosphates to extend a 3' hydroxyl group of a nucleic acid molecule, if that molecule has hybridized to a suitable template nucleic acid molecule. Polymerase enzymes are discussed in Watson, J. D., In: *Molecular Biology of the Gene,* 3rd Ed., W. A. Benjamin, Inc., Menlo Park, Calif. (1977), which reference is incorporated herein by reference, and similar texts. For amplification purposes, a preferred DNA polymerase is Taq polymerase (Cetus). Other polymerases such as the large proteolytic fragment of the DNA polymerase I of the bacterium *E. coli,* commonly known as "Klenow" polymerase, *E. coli* DNA polymerase I, and bacteriophage T7 DNA polymerase, may also be used to perform the method described herein.

Conditions or agents which increase the rate or the extent of priming, primer elongation, or strand displacement, may increase the extent of the amplification obtained with the methods of the present invention. For instance, the addition of helicases or single-stranded nucleic acid binding proteins may increase the strand displacement rate of a DNA polymerase, or may allow the use of a DNA polymerase that might not ordinarily give substantial amplification.

All of the enzymes used in an amplification reaction may be active under the same reaction conditions. Indeed, buffers exist in which all enzymes are near their optimal reaction conditions. It is desirable to provide to the reaction mixture an amount of required co-factors such as $Mg^{++}$, and dATP, dCTP, dGTP, dTTP, ATP, CTP, GTP, UTP or other nucleoside triphosphates in sufficient quantity to support the degree of amplification desired. Equivalent nucleoside triphosphate analogues, etc. (Piccirilli, J. A. et al., *Nature* 343:33–37 (1990) can be substituted or added to those specified above, provided that the base pairing, polymerase and strand displacing functions are not adversely affected to the point that the amplification does not proceed to the desired extent.

When defining conditions to be used in any specific embodiment of the present invention, primer mediated, target-independent reactions may occur which may reduce amplification efficiency, and should be examined during assay optimization. For this reason, primers should be chosen which cannot prime on themselves. Primers can also act as DNA templates in unusual promoter-independent transcription reactions (Krupp, G., *Nucl. Acids Res,* 17:3023–3036 (1989)). To minimize the likelihood of potential interfering reactions, candidate primers should preferably be tested in reactions which address these issues prior to their use in the amplification process.

In a preferred embodiment of the invention, the single-stranded molecules of the present invention, or amplification products thereof are detectably labelled. Any suitable means of detectable labelling may be employed; thus, the label may be an enzyme label, a fluorescent label, a radioisotopic label, a chemiluminescent label, etc. Examples of suitable enzyme labels include alkaline phosphatase, acetylcholine esterase, alpha-glycerol phosphate dehydrogenase, alkaline phosphatase, asparaginase, β-galactosidase, catalase, delta-5-steroid isomerase, glucose oxidase, glucose-6-phosphate dehydrogenase, glucoamylase, glycoamylase, luciferase, malate dehydrogenase, peroxidase, ribonuclease, staphylococcal nuclease, triose phosphate isomerase, urease, and yeast-alcohol dehydrogenase. Examples of suitable fluorescent labels include a fluorescein label, an isothiocyanate label, a rhodamine label, a phycoerythrin label, a phycocyanin label, an allophycocyanin label, an o-phthaldehyde label, a fluorescamine label, etc. Examples of suitable chemiluminescent labels include a luminal label, an isoluminal label, an aromatic acridinium ester label, an imidazole label, an acridinium salt label, an oxalate ester label, a luciferin label, an aequorin label, etc.

II. The Preferred Method of the Invention

As indicated, the invention accomplishes the generation of single-stranded molecules through the use of primer molecules that contain exonuclease resistant nucleotide derivatives, most preferably phosphorothioate deoxyribonucleotide or ribonucleotide derivatives. Any of a variety of chemical methods may be used to produce such phosphorothioate derivatives (see, for example, Zon, G. et al., *Anti-Canc. Drug Des.* 6:539–568 (1991); Kim, S. G. et al., *Biochem. Biophys. Res. Commun.* 179:1614–1619 (1991); Vu, H. et al., *Tetrahedron Lett.* 32:3005–3008 (1991); Taylor, J. W. et al., *Nucl. Acids Res.* 13:8749–8764 (1985); Eckstein, F. et al., *Biochemistry* 15:1685–1691 (1976); Ludwig, J. et al., *J. Org. Chem.* 54:631–635 (1989)). Phosphorothioate nucleotide derivatives can also be obtained commercially from Amersham or Pharmacia.

In the most preferred embodiment, the phosphorothioate derivative is included in the primer. Preferably, the primer molecules will be approximately 25 nucleotides in length, and contain from about 4%–to about 100%, and more preferably from about 4%–to about 40%, and most preferably about 16%, phosphorothioate residues (as compared to total residues). The nucleotides may be incorporated into any position of the primer, and may be adjacent to one another, or interspersed across all or part of the primer. Most preferably, however, the phosphorothioate residues will be adjacent to one another, and will be incorporated at the 5' terminus of the primer.

In one embodiment, the present invention can be used in concert with an amplification protocol, for example, PCR. In this embodiment, it is preferred to limit the number of phosphorothioate bonds of the primers to about 10 (or approximately half of the length of the primers), so that the primers can be used in a PCR reaction without any changes to the PCR protocol that has been established for non-modified primers. When the primers contain more phosphorothioate bonds, the PCR conditions may require adjustment, especially of the annealing temperature, in order to optimize the reaction. Incorporation of less than 4 phosphorothioates leads to incomplete exonuclease protection. The use of primers that contain 4 phosphorothioate bonds is, therefore, preferred.

The incorporation of such nucleotide derivatives into DNA or RNA can be accomplished enzymatically, using a DNA polymerase (Vosberg, H. P. et al., *Biochemistry* 16:3633–3640 (1977); Burgers, P. M. J. et al., *J. Biol. Chem.* 254:6889–6893 (1979); Kunkel, T. A., In: *Nucleic Acids and Molecular Biology*, Vol. 2, 124–135 (Eckstein, F. et al., eds.), Springer-Verlag, Berlin, (1988); Olsen, D. B. et al., *Proc. Nat., Acad. Sci. (U.S.A.)* 87:1451–1455 (1990); Griep, M. A. et al., *Biochemistry* 29:9006–9014 (1990); Sayers, J. R. et al., *Nucl. Acids Res.* 16:791–802 (1988)). Alternatively, phosphorothioate nucleotide derivatives can be incorporated synthetically into an oligonucleotide (Zon, G. et al., *Anti-Canc. Drug Des.* 6:539–568 (1991)).

The primer molecules are permitted to hybridize to a complementary target nucleic acid molecule, and are then extended, preferably via a polymerase, to form an extension product. The presence of the phosphorothioate nucleotides in the primers renders the extension product resistant to nuclease attack. As indicated, the amplification products containing phosphorothioate or other suitable nucleotide derivatives are substantially resistant to "elimination" (i.e. degradation) by 5'→3' exonucleases such as T7 exonuclease or λ exonuclease, and thus a 5'→3' exonuclease will be substantially incapable of further degrading a nucleic acid molecule once it has encountered plurality of phosphorothioate residues (most preferably, about 4 (i.e. 3–5). The use of additional numbers of phosphorothioate residues is equivalent to the use of four such residues.

Since the target molecule lacks nuclease resistant residues, the incubation of the extension product and its template—the target—in the presence of a 5'→3' exonuclease results in the destruction of the template strand, and thereby achieves the preferential production of the desired single strand.

III. Uses of the Single-Stranded Molecules Generated by the Present Invention

A. Hybridization Substrates

As indicated, the target molecule can be either single-stranded or double-stranded, and can be either DNA or RNA. Although the method of the present invention is capable of generating a single molecular species upon the amplification of a double-stranded molecule, there is no constraint on which of the strands is to be amplified. Because methods, such as PCR, result in the amplification of double-stranded molecules regardless of whether the source target molecule was initially single-stranded or double-stranded, the present invention permits either strand of an initial double-stranded molecule to be generated. Similarly, either the initial strand of a single-stranded molecule, or either the complement of that strand can be generated by the method of the present invention.

Thus, for example, the present invention can be used to either form cDNA corresponding in sequence to an mRNA molecule, or it can be used to generate an "antisense" molecule, capable of hybridizing to that mRNA molecule. "Antisense" molecules may be used to detect and identify pathogens (either viral or bacterial) in tissue (including blood, spinal fluid, tumorous tissue, etc.), food, water, milk, etc. They may also be used to evaluate the persistence or significance of latent viral or bacterial infection. In one embodiment of such a use, the single-stranded molecules generated by the invention are preferably detectably labeled, and used as hybridization probes of the target molecule. In another embodiment, the single-stranded molecules of the present invention (either labelled or unlabelled) can be amplified, using PCR, or other means, to produce amplification products that have been detectably labelled. Since such labelling can, if desired, be incorporated throughout the amplification product, this embodiment permits a higher specific activity of labelling than is obtainable through end-labelling.

The therapeutic use of antisense molecules derives from the capacity of such molecules, if incorporated into a cell, to hybridize to an mRNA molecule of complementary sequence, and thereby impair (i.e. attenuate or prevent) the translation of that mRNA molecule into a gene product. To act as an antisense oligonucleotide, the nucleic acid molecule must be capable of binding to or hybridizing with that portion of target mRNA molecule (or gene) which mediates the translation of the target mRNA.

The single-stranded nucleic acid molecules generated by the presently disclosed method can also be used to obtain oligonucleotides, such as are employed in oligonucleotide-based diagnostic assays of nucleic acid sequence variation, and in particular, the "Genetic Bit Analysis" ("GBA™") method disclosed by Goelet, P. et al. (WO 92/15712, herein incorporated by reference). GBA™ is a method for detecting single nucleotide genetic polymorphisms in nucleic acid samples that relies on a rapid, non-radioactive, solid-phase assay procedure. In essence, locus-specific DNA primers are coupled to a solid phase and hybridized to genomic templates, then extended, preferably by Klenow or T7 DNA polymerases in a sequence-directed fashion; the substrates for this chain-extension reaction are preferably novel chain terminating dideoxynucleotides having a covalently attached biotin moiety. The particular base(s) incorporated in a given reaction can then be read via a colorimetric reaction using commercially available enzyme conjugates. The reactions have been adapted to an ELISA-like 96-well format and automated using standard robotic liquid handling systems.

Modern gene mapping strategies rely on the accumulation of informative genetic markers at closely-spaced intervals along a genome. One of the advantages of GBA™ is that its use of standard reaction conditions enables tests for newly-defined single nucleotide polymorphisms to be readily developed. GBA™ also allows preliminary allelic frequencies in a population to be rapidly determined so that the informativeness of a new marker can be conveniently assessed.

Thus, in GBA™, purified oligonucleotides having a defined sequence (complementary to a target molecule) are bound to a solid support. A sample, suspected to contain the target molecule is placed in contact with the support, and any target molecules present are permitted to hybridize to the bound oligonucleotide. In one embodiment, the 5' terminus of the oligonucleotide is attached to the solid support, as described, for example by Nickerson et al. (*Proc. Natl, Acad. Sci. (U.S.A.)* 87:8923–8927 (1990)), such that the 3' end can serve as a substrate for primer extension. The presence of the desired molecule is determined by the incorporation of a labelled nucleotide to the 3' terminus of the bound oligonucleotide by a primer-dependent polymerase.

The methods of the present invention can be used to prepare modified single-stranded oligonucleotides including oligonucleotides modified for the attachment of detectable reporter groups or oligonucleotides modified for attachment to a solid support matrix (Ruth, J. L., U.S. Pat. No. 4,948, 882)).

The method of the present invention provides several salient advantages. The present invention provides a highly convenient and reliable method for preparing full-length, or partial length, single-stranded DNA molecules following the synthesis of double-stranded DNA molecules by a primer-directed nucleic acid amplification reaction, e.g., PCR. Significantly, the degradation of the nuclease sensitive strand can be carried out without prior isolation or purification of the double-stranded PCR amplification product.

In contrast to the previously discussed method of Higuchi, R. G. et al., which typically gives only 50–70% conversion, even when excess λ exonuclease is used, the method of the present invention typically yields fully quantitative degradation of the nuclease sensitive strand.

B. Amplification

As suggested above, the method of the present invention is advantageously coupled with an in vitro amplification procedure, in order to specifically amplify a single strand of a double-stranded molecule. This aspect of the invention is illustrated below by reference to PCR, however any of the previously described amplification procedures may alternatively be used.

For this purpose, PCR is performed using two primers, only one of which has been modified to contain nuclease resistant nucleotide derivatives, such as phosphorothioate nucleotides. The resulting nuclease resistant bonds become an integral part of the "target strand" of the double-stranded PCR amplification product. In contrast, the "complement strand" of the PCR amplification product, which is formed from the primer that lacked nuclease resistant nucleotide derivatives, is sensitive of nuclease degradation. Following the PCR amplification, the double-stranded DNA product obtained will contain phosphorothioate bonds at the 5' terminus of only one strand. The use of a suitable double-strand-specific, 5'→3' exonuclease therefore converts this product to a single-stranded molecule by the selective degradation of the non-protected complement strand. The phosphorothioate bonds present in the desired strand protect it from enzymatic hydrolysis. Preferably then, after the PCR reaction the exonuclease (preferably, T7 gene 6 exonuclease) can simply be added directly to the reaction mixture and the hydrolysis of the non-protected strand can be carried out, either at room temperature or, more preferably, at 37° C. for 15–30 minutes. When the λ exonuclease is used, the reaction mixture is most preferably adjusted to a pH of 9.4 (the optimal pH of this enzyme); significantly more enzyme should be used if the complete degradation of the nuclease-sensitive strand is desired. Since λ exonuclease shows a significant preference for 5'-phosphorylated substrates over non-phosphorylated ones, the nuclease sensitive PCR primer is most preferably 5'-phosphorylated in order to obtain optimal results with this enzyme.

Thus, since the 5'→3' exonuclease causes the "complement strand" to be degraded, and a preparation of "target strand" that is substantially free of natural contaminants is obtained. The single-stranded target molecules can be used as hybridization probes, as sequencing templates, or in other applications that require single-stranded DNA.

C. Sequence Analysis

As indicated, the single-stranded molecules generated by the present invention can be used to sequence a target molecule. In one embodiment of the invention, the primer that contains the phosphorothioate nucleotide derivatives is preferably labelled, such that the extension product that is formed from the primer can be readily detected or visualized. Any suitable label, such as a radioisotope, enzyme, fluorescent moiety, chemiluminescent moiety, etc., may be used for this purpose. In an alternate embodiment, the label will be incorporated into the phosphorothioate nucleotide derivative, as through the use of a radioactive sulfur isotope (i.e. $^{35}S$). In yet another embodiment, the single-stranded molecules of the present invention (either labelled or unlabelled) can be amplified, using PCR, or other means, to produce amplification products that have been detectably labelled. As indicated above, such labelling can, if desired, be incorporated into an amplification product, obtained from PCR, or by other means, in order to obtain higher specific activity of labelling than would be obtainable through end-labelling.

Thus, the method of the invention permits the preparation of single-stranded molecules that are labelled either at its 5' terminus, or optionally, throughout the molecule. As such, the molecules can be rapidly and efficiently sequenced using the previously described Maxam-Gilbert sequencing method.

The present invention includes articles of manufacture, such as "kits." Such kits will, typically, be specially adapted to contain in close compartmentalization a first container which contains a first primer containing a phosphorothioate nucleotide derivative, and a second container which contains a second primer, not containing any phosphorothioate nucleotide derivatives, such that the two primers can be used to amplify a predetermined gene sequence. The kit may additionally contain buffers, enzymes, instructional brochures, and the like.

Having now generally described the invention, the same will be more readily understood through reference to the following examples which are provided by way of illustration, and are not intended to be limiting of the present invention, unless specified.

EXAMPLE 1

Production of Single-Stranded DNA

A single-stranded molecular species corresponding to a 257 bp region of horse genomic DNA was generated through the use of PCR and two 25 residue long primers having four phosphorothioate bonds at their 5' ends ("ps" denotes a phosphorothioate bond):

SEQ ID NO: 1   C(ps)T(ps)C(ps)C(ps)ACCCTTATGAACTCATTGAAT
SEQ ID NO: 2   T(ps)G(ps)T(ps)G(ps)TGTGCTATAAATGCCACTAAC

The phosphorothioate bonds were introduced during the automated synthesis of the oligonucleotides using the commercially available reagent tetraethyl thiuram disulfide (TETD). The phosphorothioate-modified PCR primers were purified using commercially available Oligonucleotide Purification Cartridges (OPC).

The same primers (SEQ ID NO:1 and SEQ ID NO:2) were also prepared in their non-modified form. In all PCR reactions, where generation of single-stranded product was required, one of the PCR primers was phosphorothioate-modified and the other was non-modified. PCR amplifications were carried out for 30 or 35 cycles where each cycle of amplification includes one minute denaturation, two minutes annealing at 60° C., and three minutes extension at 72° C. Following the PCR amplification, a dilution of T7 gene 6 exonuclease (approximately 16 units of enzyme for 100 μl of PCR reaction) was added and the mixture incubated for 15 minutes at 37° C. The reaction was stopped by the addition of EDTA to 10 mM and analyzed by polyacrylamide gel electrophoresis.

The PCR amplification resulted in the exponential amplification of the 257 base pair sequence separating the respective primer binding sites. Treatment with exonuclease resulted in the complete degradation of the nuclease sensitive strand. Electrophoretic analysis of the amplified material after exonuclease treatment revealed that the material had been converted into a 257 base long single-stranded form.

EXAMPLE 2

Stability of Phosphorothioate Bonds to Hydrolysis by T7 Gene 6 Exonuclease

The bacteriophage T7 gene 6 exonuclease hydrolyses double-stranded DNA in the 5' to 3' direction. In order to study the effect on the enzyme activity of the substitution of regular phosphodiester bonds with phosphorothioates, the following 3' biotinylated, self-complementary oligonucleotides were synthesized (45 mers; "X" indicates the presence of a phosphorothioate linkage between the adjacent nucleotides; B denotes a biotin residue):

Oligo #1 (SEQ ID NO. 3):
CCGCGTGGTGCCTGGTGCCCTTTTT
GGGCACCAGGCACCACGCGG-B

Oligo #2 (SEQ ID NO: 4):
$C_x$CGCGTGGTGCCTGGTGCCCTTTTT
GGGCACCAGGCACCACGCGG-B

Oligo #3 (SEQ ID NO: 5):
$C_xC_xG_xC_x$GTGGTGCCTGGTGCCCTTTTT
GGGCACCAGGCACCACGCGG-B Oligonucleotides #1–3 were synthesize trityl-on, purified by reversed-phase HPLC, detritylated by treatment with 80% acetic acid, and desalted. Oligonucleotide #1 does not contain phosphorothioate bonds at its 5' end. Oligonucleotide #2 contains one phosphorothioate bond at the 5' end. It is therefore a mixture of two diastereoisomers, Rp and Sp, depending upon the orientation of the phosphorothioate residue. These two diastereoisomers were well separated by reverse-phase HPLC at the trityl-on level and obtained in pure from after detritylation. The two individual diastereoisomers of oligonucleotide #2 thus obtained are referred to below as peak A (eluting earlier) and peak B (eluting later).

Oligonucleotides #1–3 were designed to form stable hairpin-type self-complementary secondary structures, with a single-stranded loop of five thymidine residues. Upon treatment with T7 gene 6 exonuclease, these oligonucleotides should be hydrolyzed from the 5' end up to the thymidine loop, and would thereby be converted to single-stranded molecules. To capture these resulting 3' biotinylated single-stranded oligonculeotides onto a solid phrase by hybridization, the oligonucleotide #4 was immobilized in 96 well plates. This oligonucleotide has the sequence:

Oligo #4 (SEQ ID NO: 6):
AGCCTCAGACCGCGTGGTGCCTGGT

The sixteen 3' terminal bases of this oligonucleotide are complementary to the 3' ends of the biotinylated oligonucleotides #1–3.

Approximately 60 pmoles of the purified oligonucleotides #1–3 were treated with either 0 or 4 units/μl of T7 gene 6 exonuclease, at 37° C. in a total volume of 100 μl. Following this treatment, aliquots were removed at intervals and mixed with an equal volume of 3M NaCl, 20 mM EDTA. After an additional dilution step in 1.5M NaCl, 10 mM EDTA, aliquots containing approx. 1 pmol of oligonucleotide were added to the wells of a 96 well plate containing the immobilized oligonucleotide #4.

The presence of absence of biotin was then detected in a colorimetric assay. This assay was performed in the following manner. After the hybridization, the plate was incubated with a 1:1200 dilution of anti-biotin horseradish peroxidase conjugate (Vector Laboratories, Burlingame, Calif.) in 1% BSA in TNTw, for 30 min at room temperature. The plate was then washed six times with TNTw and a solution of 1 mg/ml of o-phenylenediamine (OPD) in 0.1M citrate buffer, PH 4.5, containing 0.012% $H_2O_2$ was added. The plate was immediately placed in a plate reader ($v_{max}$, Molecular Devices), and the development of color was followed at 450 nm for 2 min. The results were expressed as $mOD^{450}$/min.

The results of this assay are summarized in Table 1. The signals given in this Table are those obtained after 15 min treatment with exonuclease. No increase in signal was seen upon longer incubation. Table 1 thus shows the effect of phosphorothioate residues on the activity of T7 gene 6 exonuclease.

TABLE 1

| Oligo # | Number of 5' phosphorotioate residues | Signal without exonuclease treatment | Signal after treatment with 4 u/µl of exonuclease |
|---|---|---|---|
| #1 | 0 | 4 | 196 |
| #2 peak A | 1 | 4 | 220 |
| #2 peak B | 1 | 4 | 180 |
| #3 | 4 | 5 | 6 |

Several important results emerged from these experiments. As expected, none of the self-complementary, double-stranded oligonucleotides was able to hybridize to the solid-phase immobilized oligonucleotide. Hybridization only took place if a single-stranded, biotinylated oligonucleotide was obtained by treatment with T7 gene 6 exonuclease. In this assay, oligonucleotide # 1, as well as both diasteroisomers of oligonucleotide #2 were found to be equally good substrates for the exonuclease. Thus, the presence of only one phosphorothioate residue does not provide sufficient protection. In contrast, four phosphorothioate residues at the 5' end of oligonucleotide #3 provided complete protection from the hydrolytic activity of T7 gene 6 exonuclease. Most likely, the enzyme is capable of bypassing the 5' terminal phosphorothioate bond and starting the hydrolysis from the next phosphodiester.

EXAMPLE 3

Colorimetric Detection of PCR Products in 96 Well Plates

Having established that phosphorothioate bonds can provide protection from the hydrolytic action of T7 gene 6 exonuclease, PCR primers were prepared containing four internucleotidic phosphorothioate bonds at their 5' ends. A fifth phosphorothioate bond links the 5' terminal nucleotide of these primers to a biotin residue, which allows the nonradioactive detection of the PCR products. These labeled primers were used together with unmodified opposite strand primers to amplify fragments from horse genomic DNA. The sequences of the PCR primers and capture probes are as follows:

Primer pair A
SEQ ID NO: 7:
$B_x - C_xC_xA_xA_x$AGGAGCTGGGTCTGAAACAAA
SEQ ID NO: 8:
ATGGCTTCCCACCCTACCCATCCCG The amplification product of primer pair A was 93 base pairs long, and was captured using a capture probe having the following sequence:

SEQ ID NO: 9:
TGTTCTGGGAAAGACCACATTATTT

Primer pair B:
SEQ ID NO: 10:
$B_x - A_xT_xG_xC_x$TCCCAGGTGATTCCAGTGTGC
SEQ ID NO: 11:
GGTGCTGTGCGAGGTACACTTGACTG The amplification product of primer pair B was 201 base pairs long, and was captured using a capture probe having the following sequence:

SEQ ID NO: 12:
AGAAACACAAGGCCCAAGAACAGGA

Primer pair C:
SEQ ID NO: 13:
$B_x - G_xG_xA_xT_x$CCAGATGAACAACCAGATGAA
SEQ ID NO: 14:
CTGCAGCCCACTGGGCCTTCTTTGT The amplification product of primer pair C was 547 base pairs long, and was captured using a capture probe having the following sequence:

SEQ ID NO: 15: CCTTTGTGTAGAGTAGTTCAAGGAC

For all PCR reactions, negative controls were carried out that contained all reactions components with the exception of the horse genomic DNA. A positive result of such a control reaction would indicate contamination of one of the reaction components by a previously obtained PCR product.

Following the PCR amplification, aliquots of the reaction mixtures were withdrawn and saved as double-stranded PCR controls, while the rest of the mixtures was treated with T7 gene 6 exonuclease. Analysis was then carried out using polyacrylamide gel electrophoresis and also by hybridization of the single-stranded products of the exonuclease reaction to oligonucleotide probes immobilized in 96 well plates. The capture oligonucleotides were designed to hybridize to internal regions of the PCR products, thereby eliminating the possible capture of primer-dimers. Following the hybridization step, the presence or absence of biotin was determined with a colorimetric reaction using an anti-biotin horseradish peroxidase conjugate.

The results of polyacrylamide gel electrophoretic analysis of the PCR products illustrated that the exonuclease used hydrolysed the unmodified DNA strand, and left the phosphorothioated strand intact.

To demonstrate the specificity of hybridization, each of the same three PCR products after the exonuclease treatment was hybridized to wells that contained each of the three capture oligonucleotides. Thus, the products of PCR reactions, A, B, and C were rendered single-stranded by treatment with 2 units/µl of T7 gene 6 exonuclease and aliquots corresponding to 5 µl of the initial PCR action were added to the wells of a microliter plate containing the appropriate capture oligonucleotides for hybridization. The results of the colorimetric assay are presented in $mOD_{450}$/min. All experiments were carried out in duplicate; the results shown are averages (NT=not tested, "–control"=negative control). The results of the microliter plate hybridization assay are summarized in Table 2. It should be noted that no hybridization signals were obtained using the double-stranded PCR products directly, without the exonuclease step. This again illustrates that the exonuclease used hydrolyses the unmodified DNA strand, and leaves the phosphorothioated strand intact. The results of this cross-hybridization experiment are also included in Table 2. Each of the three PCR products hybridized only to its specific capture oligonucleotide.

TABLE 2

| PCR reaction | hybridization to capture oligo for reaction | Signal without exonuclease treatment | Signal after exonuclease treatment (2 u/µl) |
|---|---|---|---|
| A | A | 2 | 450 |
|   | B | NT | 3 |
|   | C | NT | 1 |

TABLE 2-continued

| PCR reaction | hybridization to capture oligo for reaction | Signal without exonuclease treatment | Signal after exonuclease treatment (2 u/μl) |
| --- | --- | --- | --- |
| A (- control) | A | NT | 1 |
| B | A | NT | 4 |
|   | B | 1 | 630 |
|   | C | NT | 1 |
| B (- control) | B | NT | 4 |
| C | A | NT | 3 |
|   | B | NT | 1 |
|   | C | 2 | 450 |
| C (- control) | C | NT | 4 |

EXAMPLE 4

Use of Phosphorothioate PCR Primers for PCR Products Sterilization

One embodiment of the present invention concerns the placement of phosphorothioate bonds at the 3' rather than the 5' end of the PCR primers. Upon treatment with T7 gene 6 exonuclease, the 5' unmodified parts of the double-stranded PCR products will be degraded up to the phosphorothioate bonds. The resulting product can be either single-stranded or double-stranded, depending on whether only one PCR primer contained phosphorothioates, or both. In both cases, assuming a very high efficiency of the exonuclease reaction, the resulting products should not be reamplifiable in a subsequent polymerase chain reaction that uses the same primers, since the parts of the molecule where the primers should hybridize will have been destroyed. This could constitute an alternative method to preventing PCR cross-contamination.

EXAMPLE 5

Typing of DNA Single-Base Polymorphisms by GBA™.

As indicated above, Genetic Bit™ Analysis (GBA™) is a solid-phase method for the typing of single-nucleotide polymorphisms. In this method, oligonucleotide primers (called GBA™ primers) are immobilized on solid phases like polystyrene or glass, hybridized to single-stranded PCR templates obtained by the method of the present invention, and subjected to enzymatic extension at their 3' ends by a single, labeled ddNTP. The nature of the incorporated ddNTP is determined by the nucleotide that is located in the opposite strand (the polymorphic nucleotide). This assay can be conveniently carried out in polystyrene ELISA plates, on polystyrene pins, or on glass slides. A typical example of GBA™ carried out in a polystyrene plate is given below. In this example, GBA™ is used to type a diallelic polymorphism in equine genomic DNA.

The use of phosphorothioate-containing oligonucleotides in GBA™ is illustrated by the use of PCR primers to amplify a 112 bp region from equine genomic DNA that contains a single-base polymorphism. The PCR primers had the following sequences:

(SEQ ID NO: 16)
ATAATACAGAAGTTCTGAGAGGCTA
(SEQ ID NO: 17)
$_x$G$_x$G$_x$A$_x$TCCAGGTCTGCTTCTGCTTCCC

The PCR primer of SEQ ID NO:17 contains at its 5' end four phosphorothioate bonds. These protect this end of the double-stranded PCR product from the exonucleolytic action of the T7 gene 6 exonuclease and allow the preparation of single-stranded PCR product.

Genomic DNA isolated from four different horses was used. The amplification by PCR was carried out by standard techniques, using the oligonucleotides SEQ ID NO:16 and SEQ ID NO:17 as primers. The double-stranded PCR product was converted to the single-stranded form as described, and it was hybridized to a GBA198 primer having the following sequence:

SEQ ID NO: 5' AAGAGAAAGAGTTTTGCCTCAATCC

This GBA™ primer was immobilized on a polystyrene 96 well plate. Following the hybridization of the PCR-derived, single-stranded DNA fragment to the immobilized GBA™ primer, the 3' end of the latter was enzymatically extended by one labelled ddNTP, in the presence of the large fragment of DNA polymerase I from *E. coli* (Klenow polymerase). The extension mixture used contained the following components: 20 mM Tris-HCl, pH 7.5; 10 mM MgCl$_2$; 25 mM NaCl; 10 mM MnCl$_2$; 15 mm sodium isocitrate; 1.5 μM of each of three unlabeled 2', 3'-dideoxynucleoside 5'-triphosphates and either 1.5 μM of biotin-labelled 2', 3'-dideoxyadenosine 5'-triphosphate or 1.5 μM of biotin-labelled 2', 3'-dideoxyguanosine 5'-triphosphate; and 0.15 units of the Klenow polymerase per well. The extension was carried out in separate wells, each containing a different labeled ddNTP. The presence of biotin was then revealed by a colorimetric detection as described above. The results of this experiment are shown in Table 3.

TABLE 3

| Horse # | mOD$_{450}$/min Base A | mOD$_{450}$/min Base G | Genotype |
| --- | --- | --- | --- |
| 1 | 115 | 80 | AG |
| 2 | 2 | 150 | GG |
| 3 | 75 | 90 | AG |
| 4 | 85 | 1 | AA |

These results show that, for this polymorphism, horses 1 and 3 are heterozygotes, horse 2 is a G homozygote, and horse 4 is an A homozygote.

The GBA™ (genetic bit analysis) method is thus a simple, convenient, and automatable genotyping method. In this method, sequence-specific annealing to a solid phase-bound primer is used to select a unique polymorphic site in a nucleic acid sample, and interrogation of this site is via a highly accurate DNA polymerase reaction using a set of novel non-radioactive dideoxynucleotide analogs. One of the most attractive features of the GBA™ approach is that, because the actual allelic discrimination is carried out by the DNA polymerase, one set of reaction conditions can be used to interrogate many different polymorphic loci. This feature permits cost reductions in complex DNA tests by exploitation of parallel formats and provides for rapid development of new tests.

The intrinsic error rate of the GBA™ procedure in its present format is believed to be low; the signal-to-noise ratio in terms of correct vs. incorrect nucleotide incorporation for homozygotes appears to be approximately 20:1. GBA™ is thus sufficiently quantitative to allow the reliable detection of heterozygotes in genotyping studies. The presence in the DNA polymerase-mediated extension reaction of all four dideoxynucleoside triphosphates as the sole nucleotide substrates heightens the fidelity of genotype determinations by suppressing misincorporation. GBA™ can be used in any application where point mutation analyses are presently employed—including genetic mapping and linkage studies, genetic diagnoses, and identity/paternity testing—assuming that the surrounding DNA sequence is known.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for generating a desired single-stranded nucleic acid molecule, substantially free of any nucleic acid molecule of complementary sequence, said method comprising the steps:

A) incubating a preselected nucleic acid molecule in the presence of a primer molecule; wherein said primer molecule is capable of hybridizing to said preselected molecule, and wherein said primer molecule contains a region of at least four phosphorothioate nucleotide residues at said primer's 5' terminus;

B) permitting template-dependent extension of said primer to thereby form said desired nucleic acid molecule; and C) adding to said incubation a 5'→3' exonuclease selected from the group consisting of T7 5'→3' exonuclease and lambda 5'→3' exonuclease, under conditions sufficient to eliminate said preselected molecule, and to thereby generate said desired single-stranded molecule substantially free of any nucleic acid molecule of complementary sequence.

2. The method of claim 1, wherein in step B, after forming said desired nucleic acid molecule, said molecule is incubated in the presence of a second primer molecule capable of hybridizing thereto, and of being extended in a template-dependent manner to thereby form a nucleic acid molecule having a sequence substantially complementary to that of said desired molecule.

3. The method of claim 1, wherein in step B, after forming said desired nucleic acid molecule, said molecule is incubated in the presence of a second primer molecule capable of hybridizing thereto, and with at least one dideoxynucleotide derivative, but in the absence of any non-terminating deoxynucleotide derivatives; wherein said incubation is under conditions sufficient to permit the extension of said primer in a template-dependent manner.

4. The method of claim 1, wherein said primer has a length of from about 10 to about 30 nucleotides.

5. The method of claim 4, wherein said primer has a length of from about 20 to about 25 nucleotides.

6. The method of claim 1, wherein the exonuclease resistance of said region that is resistant to a 5'→3' exonuclease is caused by a plurality of phosphorothioate nucleotide derivatives.

7. The method of claim 1, wherein said primer is detectably labelled.

8. The method of claim 7, wherein said nucleotide that confers 5'→3' exonuclease resistance to said primer molecule is detectably labelled.

9. The method of claim 1, wherein said detectable label is selected from the group consisting of an enzyme label, a fluorescent label, a radioisotopic label, and a chemiluminescent label.

10. The method of claim 1, wherein said desired single-stranded nucleic acid molecule is detectably labelled by the incorporation of labelled nucleotides during the template-dependent extension of the primer.

11. The method of claim 10, wherein said detectable label is selected from the group consisting of an enzyme label, a fluorescent label, a radioisotopic label, and a chemiluminescent label.

12. A method for detecting a desired exonuclease resistant amplification product of a polymerase chain reaction which comprises:

A) conducting a polymerase chain reaction with two primer molecules, wherein one of said primer molecules contains a region of at least four phosphorothioate nucleotide residues at said primer's 5' terminus; said reaction being sufficient to form double-stranded amplification products;

B) subsequently treating said amplification products with a 5'→3' exonuclease selected from the group consisting of T7 5'→3' exonuclease and lambda 5'→3' exonuclease, under conditions to degrade oligonucleotides that lack a sufficient number of phosphorothioate bonds to render said oligonucleotides resistant to said exonuclease;

C) detecting said desired amplification product of said polymerase chain reaction by permitting said product to hybridize to a complementary oligonucleotide bound to a solid support.

13. A kit, being specially adapted to contain in close compartmentalization a first container which contains a first primer, said first primer containing a region of at least four phosphorothioate nucleotide residues at said primer's 5' terminus; and a second container which contains a second primer lacking any phosphorothioate nucleotide derivatives, such that the two primers can be used to amplify a predetermined gene sequence.

14. The kit of claim 13 which additionally includes a 5'→3' exonuclease selected from the group consisting of T7 5'→3' exonuclease and lambda 5'→3' exonuclease.

* * * * *

UNITED STATES PATENT AND TRADEMARK OFFICE
CERTIFICATE OF CORRECTION

PATENT NO. : 5,518,900  
DATED : May 21, 1996  
INVENTOR(S) : Nikiforov et al.

Page 1 of 1

It is certified that error appears in the above-identified patent and that said Letters Patent is hereby corrected as shown below:

<u>Column 34, claim 9,</u>  
Line 17, please replace "1" with -- 7 --.

Signed and Sealed this

Eighth Day of January, 2002

Attest:

*Attesting Officer*

JAMES E. ROGAN  
*Director of the United States Patent and Trademark Office*